(12) United States Patent
Devloo (10) Patent No.: US 10,710,090 B2
(45) Date of Patent: Jul. 14, 2020

(54) CANOLA SEED SAMPLE CRUSHER

(71) Applicant: Gerard Devloo, Somerset (CA)

(72) Inventor: Gerard Devloo, Somerset (CA)

( * ) Notice: Subject to any disclaimer, the term of this patent is extended or adjusted under 35 U.S.C. 154(b) by 309 days.

(21) Appl. No.: 15/458,551

(22) Filed: Mar. 14, 2017

(65) Prior Publication Data

US 2017/0315027 A1    Nov. 2, 2017

Related U.S. Application Data

(60) Provisional application No. 62/329,000, filed on Apr. 28, 2016.

(51) Int. Cl.

| | |
|---|---|
| *B02C 4/06* | (2006.01) |
| *A01C 1/00* | (2006.01) |
| *A01C 1/04* | (2006.01) |
| *B02C 4/28* | (2006.01) |
| *B02C 4/42* | (2006.01) |
| *G01N 1/28* | (2006.01) |

(Continued)

(52) U.S. Cl.
CPC ............... *B02C 4/06* (2013.01); *A01C 1/00* (2013.01); *A01C 1/04* (2013.01); *A01C 1/042* (2013.01); *B02C 4/286* (2013.01); *B02C 4/42* (2013.01); *G01N 1/286* (2013.01); *G01N 33/02* (2013.01); *A01C 1/025* (2013.01)

(58) Field of Classification Search
CPC ........... A01C 1/042; A01C 1/025; A01C 1/04; B02C 4/06

See application file for complete search history.

(56) References Cited

U.S. PATENT DOCUMENTS

| | | | | |
|---|---|---|---|---|
| 1,311,352 A | * | 7/1919 | Jones | .......... B02C 4/32 |
| | | | | 241/225 |
| 1,364,050 A | * | 12/1920 | Gray | .......... A01C 1/042 |
| | | | | 53/397 |

(Continued)

FOREIGN PATENT DOCUMENTS

| | | | | |
|---|---|---|---|---|
| CH | 442940 A | * | 8/1967 | .......... B02C 4/06 |
| DE | 4122918 A1 | * | 1/1993 | .......... A47J 42/04 |

(Continued)

OTHER PUBLICATIONS

DE-19503971—Translation excerpt from ESPACENET.*

(Continued)

*Primary Examiner* — Teresa M Ekiert
*Assistant Examiner* — Sarkis A Aktavoukian
(74) *Attorney, Agent, or Firm* — Christopher J. Dynowski; Ade & Company Inc.; Kyle R. Satterthwaite (57) ABSTRACT

A canola seed sample crusher features a frame, and a drum rotatably carried on the frame and having an array of seed pockets on an outer periphery thereof. The seed pockets are sized and shaped to receive individual canola seeds respectively therein. A pathway is arranged to receive a length of adhesive tape and guide the tape over the seed pockets in the outer periphery of the drum during rotation thereof to adhesively collect the sample of canola seeds from the seed pockets onto the adhesive tape. A crushing mechanism is carried on the frame and operatively installed at a position along the pathway to crush the sample of canola seeds collected on the adhesive tape during passage of the tap tape through the crushing mechanism.

16 Claims, 5 Drawing Sheets

(51) Int. Cl.
  *G01N 33/02* (2006.01)
  *A01C 1/02* (2006.01)

(56) References Cited

U.S. PATENT DOCUMENTS

| | | | | | |
|---|---|---|---|---|---|
| 1,366,463 | A | * | 1/1921 | Jones | B02C 4/02 241/225 |
| 1,975,389 | A | * | 10/1934 | Cox | B02C 4/22 241/239 |
| 1,983,736 | A | * | 12/1934 | Cox | B02C 4/34 241/241 |
| 2,006,318 | A | * | 6/1935 | Schmidt | A47J 42/56 192/129 A |
| 2,156,618 | A | * | 5/1939 | Carruthers | B02C 4/22 241/240 |
| 2,360,345 | A | * | 10/1944 | Hilkemeicr | B28C 5/4237 277/353 |
| 2,374,912 | A | * | 5/1945 | Barnes | B28C 5/4237 285/189 |
| 2,507,571 | A | * | 5/1950 | Lacout | A47J 42/24 241/243 |
| 2,641,298 | A | * | 6/1953 | Kinnear, Jr. | A01C 1/042 156/279 |
| 2,764,361 | A | * | 9/1956 | Moore | B02C 13/286 241/185.5 |
| 2,797,052 | A | * | 6/1957 | Clark | B02C 4/26 241/185.5 |
| 2,807,298 | A | * | 9/1957 | Koeshall | B26D 3/18 241/199 |
| 3,282,199 | A | * | 11/1966 | Mason | B02C 4/06 100/102 |
| 3,294,045 | A | * | 12/1966 | Kelley | A01C 1/02 111/180 |
| 3,419,223 | A | * | 12/1968 | Morin | B02C 18/144 241/285.3 |
| 3,445,981 | A | * | 5/1969 | Hori | A01C 1/042 47/56 |
| 3,511,016 | A | * | 5/1970 | Craig | B65B 9/06 221/211 |
| 3,555,774 | A | * | 1/1971 | Craig | B65B 41/16 242/420.1 |
| 3,561,187 | A | * | 2/1971 | Rohnert | A01C 1/042 493/254 |
| 3,643,880 | A | * | 2/1972 | Peterson, Jr. | B02C 23/00 193/2 R |
| 3,683,583 | A | * | 8/1972 | Cochran | B65B 9/06 47/56 |
| 3,850,286 | A | * | 11/1974 | Tobin, Jr. | A01C 1/046 198/443 |
| 3,901,349 | A | * | 8/1975 | DeNoyer | G10K 11/172 181/200 |
| 3,999,358 | A | * | 12/1976 | Lewis | A01C 1/042 53/450 |
| 4,015,784 | A | * | 4/1977 | Hughes | A22C 5/00 241/162 |
| 4,089,478 | A | * | 5/1978 | Collie | B02C 4/06 241/167 |
| 4,140,284 | A | * | 2/1979 | Jobkes | B02C 13/095 241/189.1 |
| 4,200,243 | A | * | 4/1980 | Peterson, Jr. | B02C 18/148 241/224 |
| 4,266,502 | A | * | 5/1981 | Monaco | A23G 3/2076 118/16 |
| 4,282,985 | A | * | 8/1981 | Yamamoto | A01C 7/04 111/152 |
| 4,736,896 | A | * | 4/1988 | Wagner | B02C 18/302 241/82.1 |
| 4,905,917 | A | * | 3/1990 | Fetzer | B02C 4/286 241/101.8 |
| 4,925,117 | A | * | 5/1990 | Ramos | B02C 19/0081 241/100 |
| 4,926,583 | A | * | 5/1990 | Hamilton | A01C 7/044 111/179 |
| 5,000,391 | A | * | 3/1991 | LaPointe | B02C 18/148 241/285.2 |
| 5,102,059 | A | * | 4/1992 | Nyberg | B02C 18/145 241/243 |
| 5,174,511 | A | * | 12/1992 | Ruegger | B02C 4/286 241/224 |
| 5,246,176 | A | * | 9/1993 | Fetzer | B02C 4/286 100/173 |
| 5,553,797 | A | * | 9/1996 | Axelsson | B02C 18/148 241/285.3 |
| 5,697,561 | A | * | 12/1997 | Plank | F25C 5/046 241/100 |
| 5,803,143 | A | * | 9/1998 | Willis | B27L 11/002 144/172 |
| 5,823,452 | A | * | 10/1998 | Ballew | B02C 4/06 241/225 |
| 6,129,296 | A | * | 10/2000 | Campbell | B02C 4/06 241/225 |
| 6,405,949 | B1 | * | 6/2002 | Maguire | B02C 18/148 241/242 |
| 7,490,565 | B2 | * | 2/2009 | Holly | A01C 7/044 111/174 |
| 8,353,471 | B2 | * | 1/2013 | Karlsson | F16M 5/00 241/1 |
| 2003/0145738 | A1 | * | 8/2003 | Bowen | B02C 4/06 99/353 |
| 2007/0257142 | A1 | * | 11/2007 | Chapman | A47J 42/00 241/92 |
| 2010/0133370 | A1 | * | 6/2010 | Flynn | B02C 18/0092 241/46.01 |
| 2011/0114772 | A1 | * | 5/2011 | Nickel | B02C 4/286 241/222 |
| 2011/0185923 | A1 | * | 8/2011 | Lee | B26F 1/42 100/176 |
| 2012/0031315 | A1 | * | 2/2012 | Beaujot | A01C 7/04 111/174 |
| 2015/0129697 | A1 | * | 5/2015 | Berglitsch | B02C 18/2233 241/220 |

FOREIGN PATENT DOCUMENTS

| | | | | |
|---|---|---|---|---|
| DE | 29607241 | U1 * | 6/1996 | B02C 4/06 |
| DE | 19503971 | A1 * | 8/1996 | B02C 1/042 |
| FR | 609583 | A * | 8/1926 | B02C 4/06 |
| FR | 654562 | A * | 4/1929 | B02C 4/06 |
| FR | 1545100 | A * | 11/1968 | A01C 1/042 |
| FR | 2174531 | A5 * | 10/1973 | A01C 1/042 |
| GB | 113674 | A * | 3/1918 | B65B 25/02 |
| GB | 563668 | A * | 8/1944 | B02C 4/04 |
| GB | 1268981 | A * | 3/1972 | A01C 1/042 |
| JP | 4890653 | B1 * | 3/2012 | |

OTHER PUBLICATIONS

DE-29607241—Machine translation of specification from Google Translate.*
Machine Translation of JP-4890653-B1 (Year: 2012).*
DE-19503971—Translation excerpt from ESPACENET, Publication Year 1996, Total pp. 9. (Year: 1996).*
DE-29607241—Machine translation of specification from Google Translate, Publication Year 1996, Total pp. 15. (Year: 1996).*

* cited by examiner

CANOLA SEED SAMPLE CRUSHER

CROSS REFERENCE TO RELATED APPLICATIONS

This application claims benefit under 35 U.S.C. 119(e) of Provisional Application Ser. No. 62/329,000, filed Apr. 28, 2016.

FIELD OF THE INVENTION

The present invention relates to a device for crushing samples of canola seeds, whereupon a count of the number of green seeds among the crushed sample can be used to gauge the quality of a particular canola crop.

BACKGROUND

In the field of agriculture, it is known that canola seed having a distinctly green colour throughout is an immature seed, and accordingly a grade or quality of a harvested canola crop can be assessed as a percentage by weight of distinctly green seeds among a sample of the harvested seeds. To accurately detect the colour throughout the seeds, it is common practice to perform a crush test, where a predetermined number of sample seeds are crushed with a hand-held roller, and the crushed state of the seeds enables a proper assessment.

To easily layout a sample of the predetermined sample size for crushing, commercially available test kits include a strip-shaped plastic tray or ruler with an array of holes laid out in a rectangular grid in a quantity matching the desired sample size. Each hole is sized and shaped to seat an individual canola seed therein, whether by dipping of the ruler into a container of canola seed or pouring of canola seed over the ruler. A length of adhesive tape is then laid adhesive-side-down over the ruler, whereupon the array of sample seeds on the ruler adheres to the tape. The separate roller is then rolled over the array of sample seeds on the adhesive side of the tape, thereby crushing the sample seeds to reveal the internal colour thereof.

The standard test procedure therefore involves several steps requiring use and manipulation of multiple tools. Accordingly, it is desirable to provide an improved or alternative solution for performing crush testing of canola seed samples.

SUMMARY OF THE INVENTION

One aspect of the invention relates to a canola seed sample crusher comprising:
a frame;
a drum rotatably carried on the frame and having an array of seed pockets on an outer periphery thereof, said seed pockets being sized and shaped to receive an individual canola seed in each pocket;
a pathway arranged to receive a length of adhesive tape and guide said length of adhesive tape over the seed pockets in the outer periphery of the drum during rotation thereof to adhesively collect the sample of canola seeds from said seed pockets onto said adhesive tape; and
a crushing mechanism carried on the frame and operatively installed at a position along said pathway to crush the sample of canola seeds collected on said adhesive tape during passage thereof through the crushing mechanism.

Preferably a seed hopper is carried on the frame and has an inlet through which a volume of canola seeds is receivable therein, and an outlet positioned to direct said volume of canola seeds toward the outer periphery of the drum, where the sample of canola seeds collect in the seed pockets thereof.

Preferably the seed hopper is movable between a useful position placing its outlet proximate the outer periphery of the drum, and a dumping position withdrawn away from the drum to release unused seeds from the hopper.

Preferably the hopper is biased into the useful position.

Preferably a tape wheel is rotatably carried on the frame for rotatably carrying a roll of adhesive tape from which said length of adhesive tape is deployed.

Preferably a tape cutter is positioned proximate the crushing mechanism at an outlet side thereof to cut free an area of the adhesive tape that carries the crushed seed sample thereon.

Preferably a press wheel is rotatably carried on the frame with an outer periphery of the press wheel positioned to urge the adhesive side of the adhesive tape into contact with the sample of canola seed in the seed pockets.

Preferably the crushing mechanism comprises a pair of crushing rollers rotatably carried on the frame in counter-rotating relation to one another with outer peripheries of said crushing rollers in contact or close proximity across the pathway to define a nip through which the adhesive tape is passed to crush the sample of canola seeds thereon.

Preferably a common drive mechanism is shared by the rotatable drum and the crushing mechanism.

Preferably the common drive mechanism comprises a flexible drive member entrained about respective roller elements of the drum and the crushing mechanism.

Preferably a hand crank is operably connected to the drum for manually driven rotation thereof.

Preferably the hand crank is operably connected to the crushing mechanism for manually driven operation thereof.

Preferably the hand crank is attached to a rotational shaft of the crushing mechanism for direct drive thereof.

Preferably the hand crank is indirectly coupled to the drum for manually driven rotation thereof simultaneously with the crushing mechanism.

Preferably the hand crank is operatively connected to the drum by the flexible drive member entrained about the respective roller elements on rotational shafts of said hand crank and said drum.

Preferably the flexible drive member is a chain and the respective roller elements are sprockets.

Another aspect of the invention relates to a canola seed sample crusher comprising:
a frame;
a drum rotatably carried on the frame and having an array of seed pockets on an outer periphery thereof, said seed pockets being sized and shaped to receive individual canola seeds respectively therein;
a seed hopper carried on the frame and having an inlet through which a volume of canola seeds is receivable therein, and an outlet positioned to direct said volume of canola seeds toward the outer periphery of the drum, where a sample of said canola seeds collect in the seed pockets thereof;
a tape wheel rotatably carried on the frame for carrying a roll of adhesive tape thereon;
a press wheel rotatably carried on the frame with an outer periphery of the press wheel in cooperating relation to the outer periphery of the drum; and a pair of crushing rollers rotatably carried on the frame in counter-rotating relation to one another with outer peripheries of said crushing rollers in close proximity or contact to define a nip therebetween;

wherein the drum, tape wheel, press wheel and crushing rollers are positioned so as to accept passage of a length of adhesive tape from the tape wheel on a pathway passing between the press wheel and the drum with an adhesive side of said tape facing the drum periphery to adhesively withdraw the sample of canola seeds from the seed pockets onto said length of tape, and extending onward through the nip of the crushing rollers for crushing of said sample of canola seeds by counter-rotation of the crushing rollers.

Any of the preferable or optional features listed above in relation to the first aspect of the invention may likewise be employed in relation to the second aspect of the invention.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
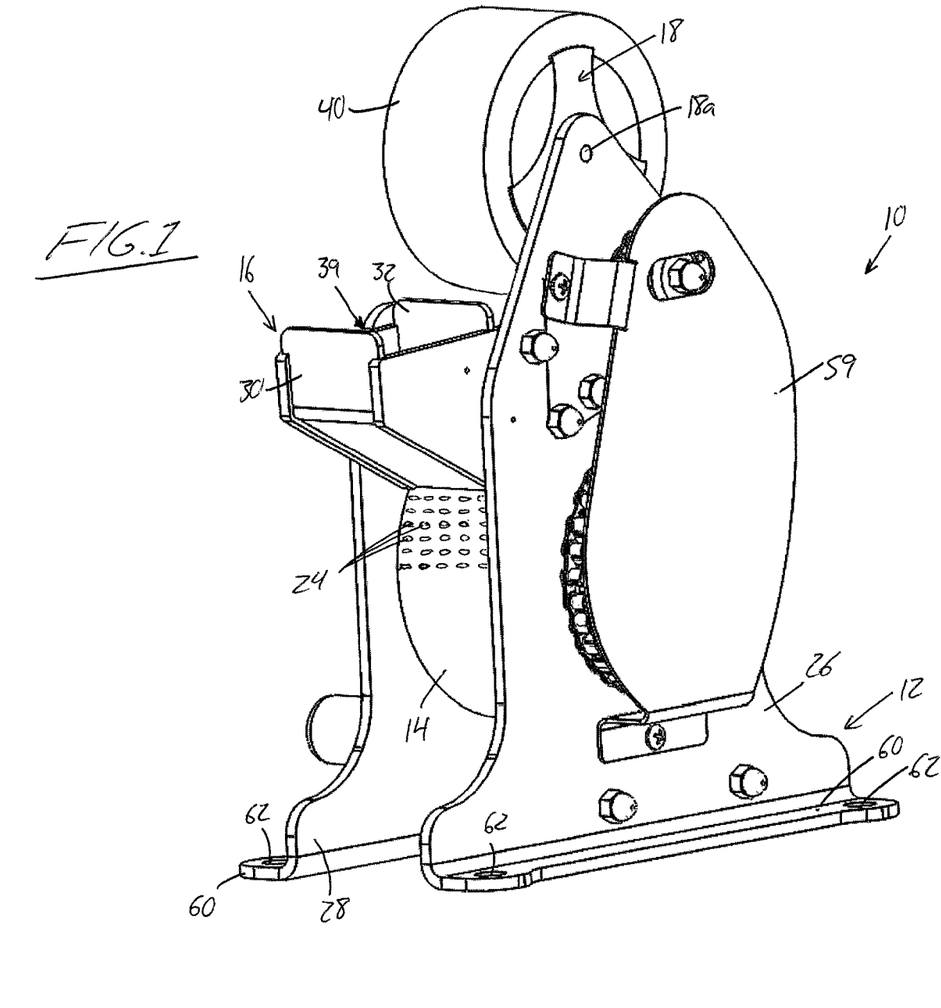
FIG. 1 is a rear perspective view of a canola seed sample crusher of the present invention from a right side thereof.
Figure 2:
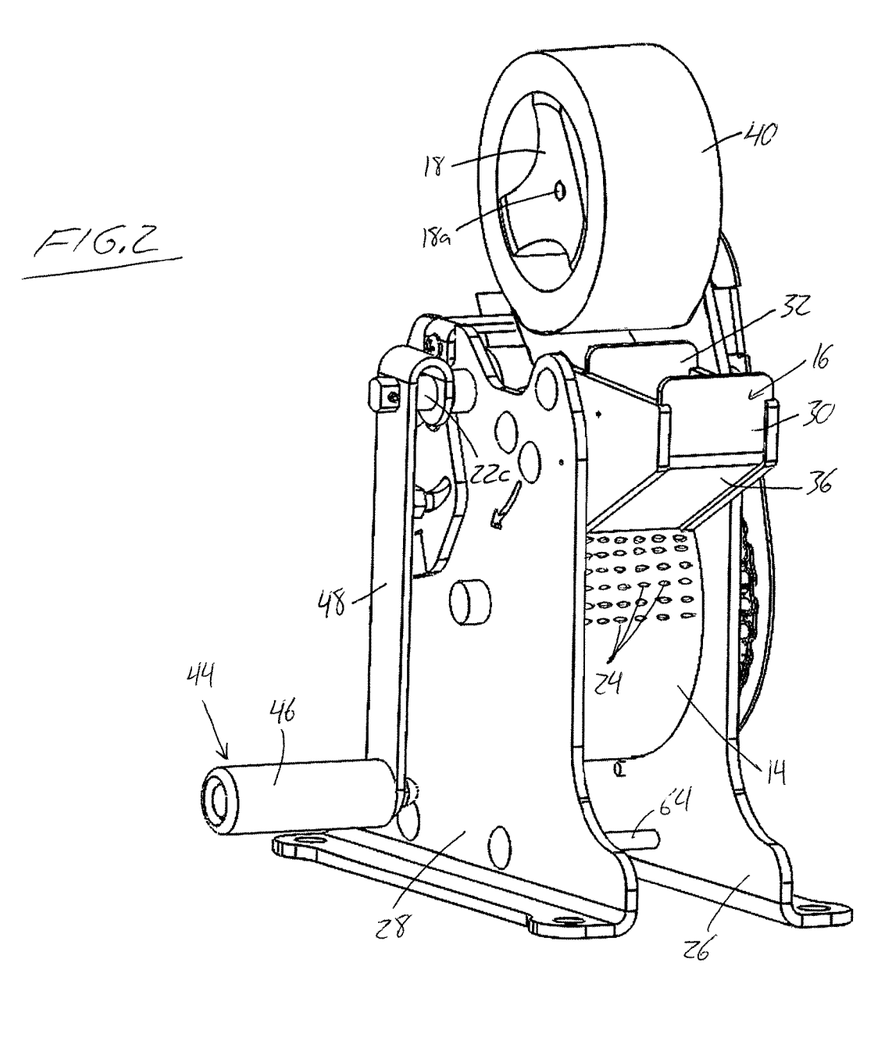
FIG. 2 is a rear perspective view of the canola seed sample crusher of FIG. 1 from a left side thereof.

The canola sample tester 10 of the illustrated embodiment of the present invention is made up primarily of a frame 12, a rotatable drum 14, a seed hopper 16, a rotatable tape wheel 18, a rotatable press wheel 20, and a pair of crushing rollers 22, 23 supported in counter-rotational relationship with one another. The drum has an array of seed pockets 24 defined in a partial circumferential area of the drum's outer periphery thereof to pick up a predetermined sample size of canola seeds from the hopper as this area moves past the hopper. As more clearly shown in FIGS. 1 and 2, the rows of the array extend generally axially of the drum, that is generally in the direction of a drum axis defined by shaft 14a (FIG. 3), and the rows of the array are substantially uniformly spaced from each other in a circumferential direction of the drum such that the array extends across the outer periphery of the drum in the circumferential direction thereof. Also, as more clearly shown in the aforementioned figures, each row of the array has a plural number of the seed pockets 24. Furthermore, as more clearly shown in the aforementioned figures, a remainder of the drum's outer periphery which is free of the seed pockets has a larger circumferential span than the spacing between adjacent rows of the array. A length of adhesive tape fed off of a roll on the tape wheel passes between the press wheel and the drum with the adhesive side of the tape facing the drum so that the sample of canola seeds in the see pockets of the drum are adhered to the tape as each row of seeds in array passes the roller. The tape continues onward between the pair of counter-rotating crushing rollers, where the array of sample seeds now adhered to the tape are crushed row-by-row as they move through the nip of these crushing rollers. Each and every step of a canola seed sample crush test, including organization of the seeds into a grid layout of predetermined size, adherence of the sample seeds to a strip of adhesive tape, and crushing of the sample seeds, are all performed through convenient use of a singular apparatus.

The frame 12 of the illustrated embodiment features a pair of parallel side walls 26, 28 standing upright in respective vertical planes that are horizontally spaced from one another. The drum 14, press wheel 20 and crushing rollers 22, 23 are all rotatably supported between the two side walls 26, 28 by way of fixed attachment to respective horizontal shafts 14a, 20a, 22a, 23a that pass through the side walls 26, 28 to define the respective rotational axes of the drum, press wheel and crushing rollers. Accordingly, each of the drum, press wheel and crushing rollers is rotatable in a vertical plane normal to its horizontal rotation axis by driven rotation of its respective shaft. The shafts 20a, 22a, 23a of the press wheel 20 and two crushing rollers 22, 23 are situated radially outward of the drum 14 in elevated positions above the two upper quadrants of the cylindrical drum. The press wheel 20 resides over a rear upper quadrant of the drum 14, while the two crushing rollers 22, 23 reside over a front upper quadrant of the drum 14. The terms front and rear are used herein only to differentiate between two opposing ends of the apparatus spaced radially outward from the rotational axis of the drum in a horizontally longitudinal direction parallel to the planes of the side walls, and not to denote any particular position or orientation in which the apparatus must reside relative to its operator or environment.

The hopper 16 is mounted at the rear end of the side walls 26, 28 above the upper rear quadrant of the drum 14 behind the press wheel 20. The hopper 16 features a vertically upright rear wall 30 and an opposing vertically upright front wall 32 that stand parallel to one another and span horizontally between two side walls 34 of the hopper. These side walls of the hopper are respectively affixed to the inner sides of the frame's two side walls 26, 28, whereby the side walls of the hopper reside in vertical planes parallel and adjacent to the side walls of the frame. The hopper's front wall 32 is taller, and reaches further downwardly than, the hopper's rear wall 30. The hopper 16 is finished off by a sloped bottom wall 36 that angles obliquely downward from a bottom end of the hopper's rear wall 30 toward the plane of the hopper's front wall 32. Here the hopper's sloped bottom wall 36 passes by the bottom end of the hopper's front wall 32 at a short distance therebeneath, as best shown in the cross-sectional view of FIG. 3. Here the sloped bottom wall 36 of the hopper continues forwardly toward, and stops just short of, the outer periphery of the drum 14. The gap left between the hopper's sloped bottom wall 36 and the bottom edge of the hopper's front wall 32 defines an outlet 38 of the hopper 16, while an open area delimited by the front, rear and side walls of the hopper at the upper ends thereof denotes an inlet 39 of the hopper.

During use of the apparatus, canola seed is loaded into the hopper by a user through the inlet 39 at the topside of the hopper 16, and the sloped bottom wall 36 of the hopper 16 gravitationally feeds the canola seed to the periphery of the drum 14 at the upper rear quadrant thereof. Accordingly, when the drum 14 is rotated in a working direction W that moves the periphery of the drum upwardly and forwardly past the outlet of the hopper, canola seeds from the hopper 16 fall onto the periphery of the drum 14 at the rear upper quadrant thereof, where the seeds settle into the seed pockets 24 when this pocketed area of the drum's periphery moves through this quadrant.

Figure 3:
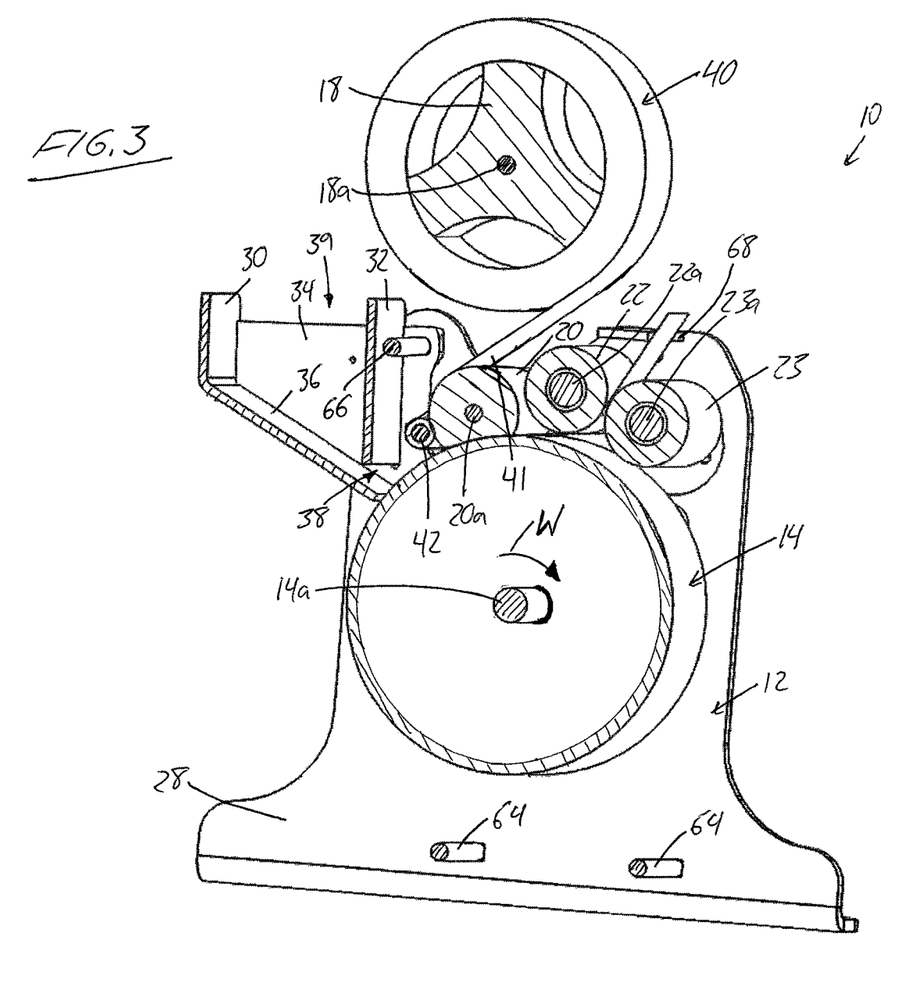
FIG. 3 is a cross-sectional view of the canola seed sample crusher of FIG. 1 through a longitudinal mid-plane thereof.

The first side wall 26 of the frame 12 is taller than the opposing second side wall 28, and the tape wheel 18 is rotatably supported on the taller first side wall 26 by a respective rotational shaft 18a at an elevated position above the hopper 16 and the shorter second side wall 28 of the frame. A roll 40 of adhesive tape is removably and replaceably mounted on the tape wheel 18, which may be of a conventional type commonly employed on commercially available tape guns commonly used for applying packing tape to shipping cartons. As best shown in FIG. 3, the adhesive tape 41 unwinds from the roll at the lower front quadrant thereof, from which it angles rearwardly and downwardly into the space between the front wall 32 of the hopper 16 and the press wheel 20. Here, the tape 41 wraps downwardly around the rear quadrants of a guide pin 42 that spans horizontally between the side walls 26, 28 of the frame just behind the press wheel 20 in close radial proximity to the outer periphery of the drum 14. The tape wraps under the guide pin 42, from which the tape continues forwardly and passes between the press wheel 20 and the outer periphery of the drum 14.

The press wheel 20, or at least an outer portion thereof that defines an outer peripheral surface of the press wheel, is made of a resiliently compressible material, the outer diameter of which slightly interferes with the outer peripheral surface of the drum 14 in the normal uncompressed state of the material. This is best seen by FIG. 3, where the material at the underside of the press wheel 20 can be seen to conform under compression to the outer periphery of the drum 14. The adhesive tape passes forwardly between the press wheel 20 and the drum 14 from the lower rear quadrant of the press wheel, and during the tape's passage between the press wheel and the drum 14, the resiliency of the press wheel's outer material applies pressure to the tape 41, forcing it against the outer periphery of the drum 14. The adhesive tape is single sided, and its adhesive side faces upwardly and rearwardly as the tape feeds of the roll 40 at the lower front quadrant thereof, whereby the redirection of the tape 41 about the guide pin 42 into the forward direction places the adhesive side of the tape downwardly as it travels under the press wheel 20. Accordingly, during rotation of the drum 14 in the working direction W to pick up seeds at the outlet of the hopper and convey the collected seeds forwardly from the hopper in a downstream direction of movement of the canola seeds through the apparatus, the adhesive side of the tape is pressed into firm contact with the seeds in the seed pockets of the drum by the press wheel 20, whereupon the seeds on the drum 14 become adhered to the tape.

With continued reference to the cross-section of FIG. 3, the length of adhesive tape 41 unwound from the roll 40 continues forwardly from under the press wheel 20 to reach over center of the drum 14 to the upper front quadrant thereof. Here, the tape 41 passes under the rearmost crushing roller 22 in the gap between this roller and the drum's outer periphery, and turns upwardly through the nip of the adjacent crushing rollers 22, 23. The size of the nip between the rollers is selected to be smaller than a canola seed, and the two crushing rollers 22, 23 are driven in counter-rotating relation to one another (i.e. in opposing rotational directions) so that the outer periphery of each crushing roller moves upwardly through the nip. Accordingly, this counter-rotation of the crushing rollers acts to both urge the tape 41 upwardly through the nip and off of the outer periphery of the underlying drum 14 while crushing the collection of sample seeds currently adhered to this unwound length of tape 41. As shown in FIG. 3, relative to the movement of the canola seeds through the apparatus, the crushing rollers 22, 23 are located downstream from an upper quadrant portion of the drum 14 along which the adhesive tape 41 is guided to adhesively withdraw the canola seeds from the seed pockets for collection on the adhesive tape.

The crushing rollers 22, 23 are harder and less compressible than the outer portion of the press wheel 20. The softer, more compressible press wheel will therefore encourage the tape 41 into adhesive contact with exposed sides of the seeds that reach outwardly from the pockets 24 in which the seeds are temporarily seated, but without crushing the seeds while still seated within the pockets. On the other hand, the harder peripheries of the crushing rollers 22, 23 will confidently crush each tape-carried seed passed through the nip of the rollers. Crushing the seeds while still in the pockets of the drum would be undesirable, as the crushed state of the seed may reduce its adherence to the tape, possibly resulting in less than a full sample of seeds being picked up by the tape, and leading to potential inaccuracies in calculating the percentage of immature green seeds in the sample when a user breaks off the seed-carrying piece of tape to count the green seeds thereon and divide the counted number by the expected sample size (i.e. by the number of seed pockets known to be on the drum).

Figure 4:
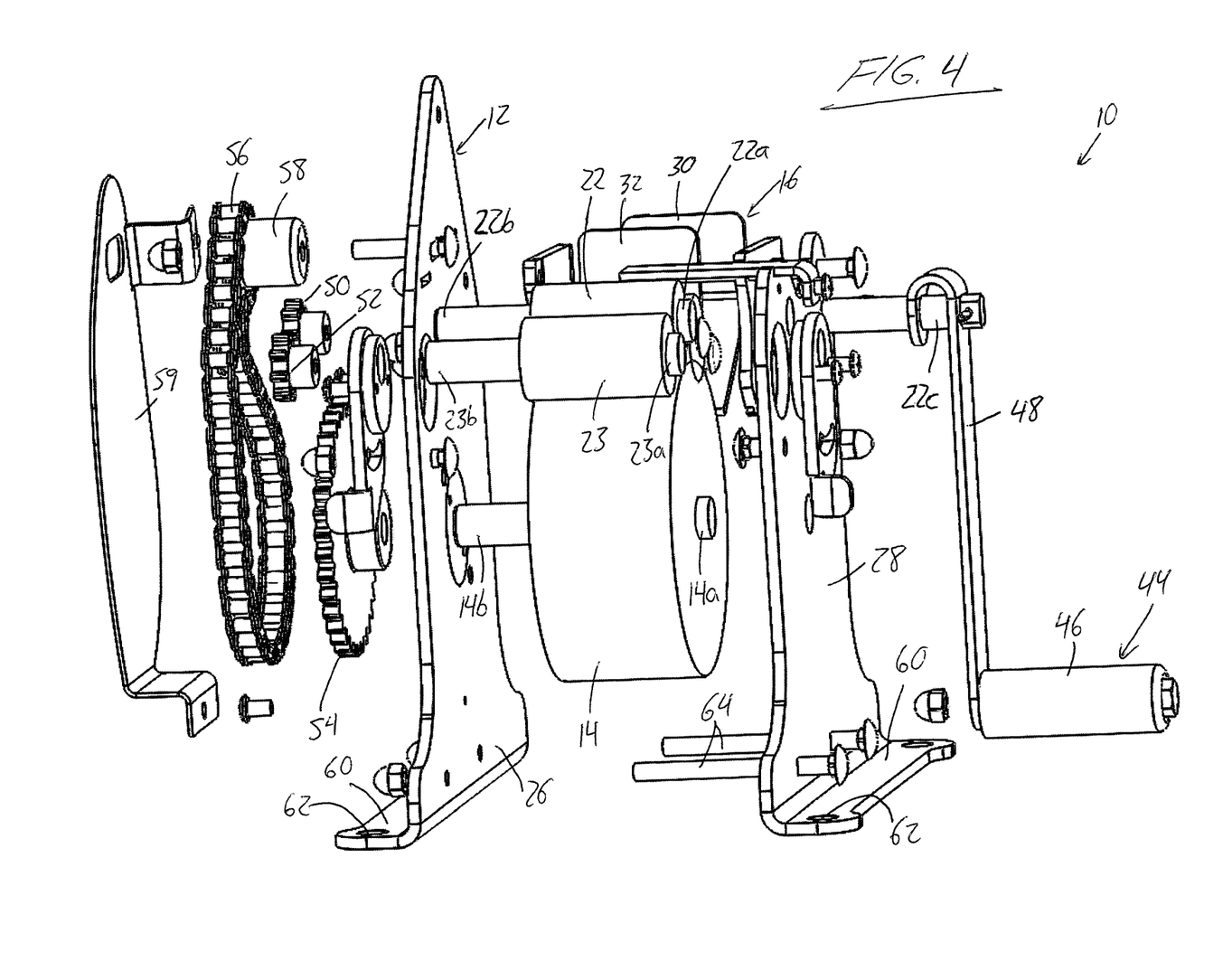
FIG. 4 is an exploded front perspective view of the canola seed sample crusher of FIG. 1.

The rotational shaft 22a of the rear crushing roller features a first projecting portion 22b that reaches outwardly from between the two side walls 26, 28 of the frame to a location laterally outward from the first side wall 26. The same rotational shaft 22a also features a second projecting portion 22c that reaches outwardly from the second side wall 28. To operate the device, a hand crank 44 features a horizontally oriented grip handle 46 rotatably pinned to a lever arm 48 that lies in a vertical plane and links the grip handle 46 to the second projecting portion 22c of the rear crushing roller's rotational shaft 22a. The first projecting portion 22b of the rear crushing roller's rotational shaft 22a on the other side of the apparatus has a first sprocket 50 affixed thereto. As shown in the exploded view of FIG. 4, the rotational shaft 22a may be assembled from two pieces, each defining a respective projecting portion of the shaft, and one of which carries the rear crushing roller 22 between the two side walls 26, 28 of the frame 12.

The rotational shaft 23a of the front crushing roller 23 likewise carries a second sprocket 52 affixed thereto at a projecting portion 23b thereof that reaches outwardly from the first side wall 26 of the frame 12. The respective sprockets 50, 52 of the two crushing rollers 22, 23 are of equal size and tooth count in order to rotate the two crushing rollers at the same rotational speed. A larger third sprocket 54 is affixed to the rotational shaft 14a of the drum at a projecting portion 14b thereof that also reaches outwardly from the first side wall 26 of the frame. Each sprocket is affixed to its respective rotational shaft for rotation therewith. A flexible drive chain 56 is entrained around all three sprockets outside the first side wall 26 of the frame, such that driven rotation of the hand crank 44 about its horizontal rotational axis (as defined by the axis of the rear crushing roller's rotational shaft 22a) drives rotation of the two crushing rollers 22, 23 and the drum 14 simultaneously. The flexible chain thus rotationally couples all three sprockets together to form a chain drive of the apparatus.

Figure 5:
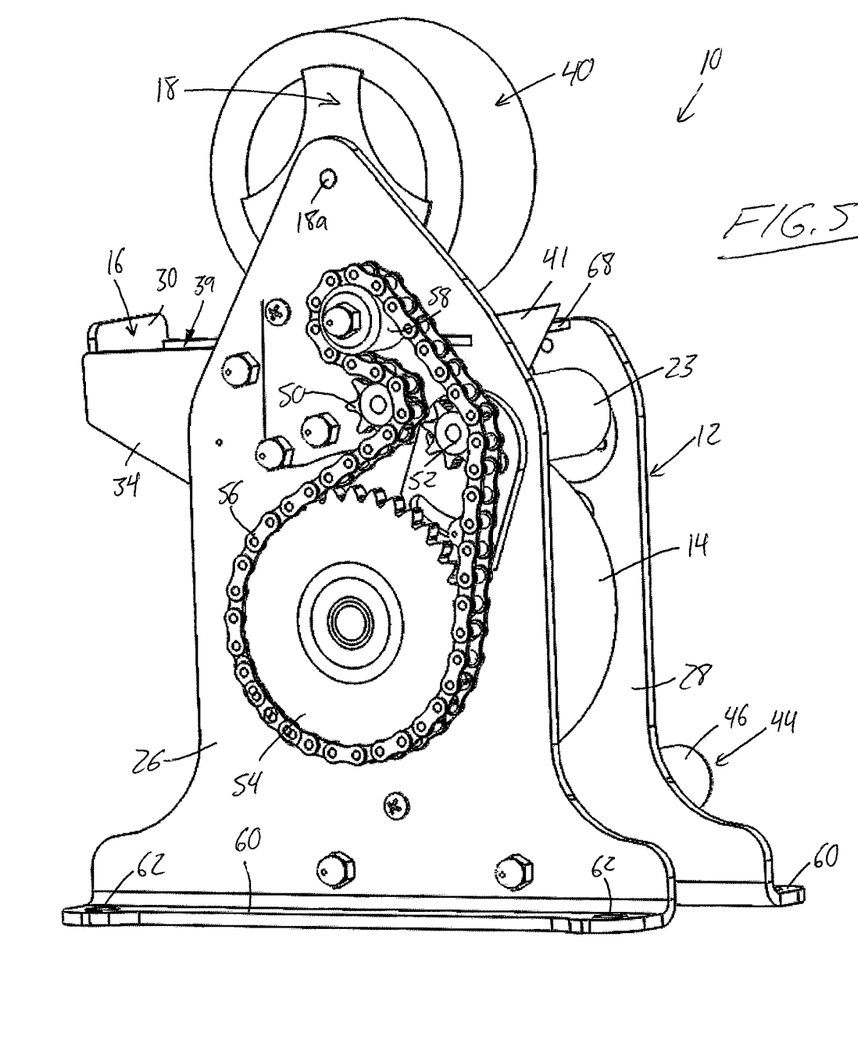
FIG. 5 is a right side perspective view of the canola seed sample crusher of FIG. 1 with a chain guard thereof removed to reveal details of a chain drive mechanism of the apparatus.

As the two crushing rollers need to rotate in opposing directions, the chain must entrain about the two respective sprockets 50, 52 in opposing directions. To accomplish this, the chain also wraps about a redirection member 58 that is carried at the outer side of the first side wall 26 of the frame 12 at a location above, and offset slightly rearward from the sprocket 50 of the rear crushing roller 22. A chain guard 59 normally mounted to the outer side of the first side wall of the frame to reside over the chain and sprockets at a distance outward from the side wall of the frame is removed in FIG. 5 to reveal the fully assembled state of the chain drive, with otherwise is only visible in the exploded view of FIG. 4. Referring to FIG. 5, the chain 56 wraps around a majority of the larger drum sprocket 54 at the underside thereof, reaches upwardly from the lower front quadrant of the drum sprocket 54 to engage about the front quadrants of the front crushing roller's sprocket 52, from which the chain continues upward and rearward to engage over the upper quadrants of the redirection member 58, where the chain is redirected downwardly and forwardly about the lower rear quadrant of the redirection member to engage downwardly around the front quadrants of the rear crushing roller's sprocket 50 before returning downwardly and rearwardly to the larger drum sprocket at the upper rear quadrant thereof.

In the illustrated embodiment, the press wheel 20 is not driven by the chain drive, and any rotation of the press wheel 20 is solely due to the frictional interface occurring between the press wheel, the tape and the drum during driven rotation of the drum by the chain drive. Likewise, the tape wheel is not driven by the chain drive, but is only rotated by tension of the tape being pulled through the apparatus by the frictional action between the press wheel and drum and between the two counter-rotating crushing rollers. When a roll of tape is fully depleted, a new roll is simply installed in its place, and the free end of the new tape is manually fed around the guide pin 42 into a feeding position pinched between press wheel 20 and the drum 14, whereupon rotation of the hand crank 44 will feed the tape 41 forwardly between the press wheel and drum to the crushing rollers 22, 23 at the upper front quadrant of the drum, where the free end of the tape will naturally be fed upward by contact with the lower rear quadrant of the front crushing roller, whose upward rotational motion will guide the tape upwardly through the crushing nip. This places the tape in a ready-condition following the above described path between the press wheel and drum, and onwardly through the nip of the crushing rollers.

While the illustrated embodiment employs a chain to drive simultaneous rotation of the drum and crushing rollers in a timed manner, other drive configurations may be employed, for example using a suitable gear train rather than chain-linked sprockets. As another option, a double sided belt may be used in conjunction with suitably notched pulleys rather than the chain and sprocket combination of the illustrated embodiment. The operation of either option is similar, where the belt or chain serves as a flexible drive member entrained about suitable rotational elements (sprockets or pulleys). The redirection element 58 may be a stationary or free-wheeling bushing, or an idler sprocket or pulley.

The frame of the illustrated embodiment employs separate side walls 26, 28 formed by respective metal brackets that also feature horizontally out-turned flanges 60 at the bottom ends of the side walls, with fastener holes 62 in these horizontal flanges 60 for receipt of bolts or screws therethrough to fasten the frame to a suitable structure at a desired site for stationary use of the apparatus. Alternate embodiments intended for portable, hand-held use may optionally forgo such stationary mounting features.

Suitable cross-members 64, for example in the form of pins or bolts, interconnect the side walls of the frame near the lower ends thereof to help maintain fixed spacing therebetween and thereby provide the frame with suitable rigidity. Another cross-pin 66 spans horizontally between the side walls just outside the front wall 32 of the hopper 16. The front wall 32 of the hopper is fixed to this cross-pin 66, which is rotatable about its horizontal axis to allow rotation of the pin and hopper relative to the frame. The cross-pin 66 thus defines a pivot point of the hopper, whereby after a seed test has been completed, the hopper outlet 38 can be tilted rearwardly away from the drum 14 about the axis of the pivot pin 66 in order to dump out any leftover seed from the hopper 16. The hopper is normally biased into its useful position placing the hopper outlet 38 at the periphery of the drum 14, whether solely by gravity or by addition of a return force by a suitable return spring (not shown). The illustrated embodiment also features a tape cutter 68 attached to and horizontally spanning between the side walls 26, 28 of the frame at a position over the crushing nip between the two crushing rollers, where the free end of the tape 41 emerges at an outlet of the roller-defined crushing mechanism. A sharpened or serrated front edge of the tape cutter 68 is therefore available for cutting free the crushed seeds on the sample carrying area of the tape after feeding thereof through the crushing rollers 22, 23.

While the illustrated embodiment employs a hand crank for manual operation, other embodiments may alternatively use a motor as the input drive source for the drum and crushing mechanism. One particular version of the apparatus may employ an array of 250 seed pockets in the drum, but this number may of course be varied. The seed pockets may be defined by through-holes in an outer cylindrical band of the drum, the through-holes being suitably sized and shaped to allow each seed to be partially recessed into a hollow interior of such a drum without falling fully through the hole. Alternatively, the seed pockets may be defined by recessed dimples that do not open fully through the drum's outer periphery into a hollow interior thereof.

In summary, the described canola seed tester is designed to produce a crushed canola sample on tape to inspect for percentage of green seed. The test is quick, convenient and smooth. The tester can replace multiple steps of processing a sample by conventional methods. First, the user drops a seed sample into hopper, and then turns the hand crank a suitable number of times to fully fill the array of seed pockets on the drum with seed transferred from the hopper's outlet opening, while rolling the tap onto the seed-filled area of the drum where the tape sticks to the seed and is gently pressed thereagainst to make better contact and ensure adequate adhesion. The seed-carrying area of the tape is transferred onward to the two crushing rollers, where the seed-carrying area of the tape emerges with a processed seed sample, fully crushed and ready for counting. The sample-carrying area of tape is torn off using the tape cutter, and thus ready for counting of the number of green seeds relative to the predetermined sample number, the division of which is used as a percentage-by-weight grading value for the quality of the sampled canola crop.

Since various modifications can be made in my invention as herein above described, and many apparently widely different embodiments of same made within the scope of the claims without departure from such scope, it is intended that all matter contained in the accompanying specification shall be interpreted as illustrative only and not in a limiting sense.

The invention claimed is:

1. A canola seed sample crusher comprising:

a frame;
a drum rotatably carried on the frame and rotatable about a horizontal rotational axis, said drum having an array of seed pockets recessed into, or opening through, an outer periphery of said drum, said seed pockets being sized and shaped to receive an individual canola seed in each pocket, said drum having an upper portion, and said upper portion having an upper quadrant portion at the outer periphery of the drum;
the array of the seed pockets comprising a plurality of rows each having a plural number of the seed pockets, each row of the array extending generally axially of the drum, and the rows being uniformly spaced from each other in a circumferential direction of the drum;
a seed hopper carried on the frame and having an outlet positioned over the upper portion of the drum to gravitationally feed the canola seeds from the seed hopper onto the outer periphery of the drum at the upper portion thereof to settle said canola seeds into the seed pockets that move through the upper portion during rotation of the drum in a forward working direction;
a pathway arranged along the upper quadrant portion of the outer periphery of the drum,
wherein the upper quadrant portion is spaced from the seed hopper in the forward working direction, such that the upper quadrant portion is downstream from the seed hopper with respect to a movement of the canola seeds,
wherein the pathway is configured to receive and guide a length of adhesive tape along the upper quadrant portion,
wherein along the pathway, the sample of canola seeds are adhesively withdrawn from the seed pockets by the adhesive tape during the rotation of the drum in the forward working;
a pair of crushers carried by the frame in opposite relation to one another and at a position along said pathway,
wherein the crushers are downstream from the upper quadrant portion to receive the adhesive tape with the canola seeds thereon between the crushers, the crushers being configured to cooperatively crush the sample of canola seeds collected on said adhesive tape during passage thereof between the crushers;
wherein the array of the seed pockets circumferentially-extends across only a partial circumferential span of the outer periphery of the drum leaving a remainder of the outer periphery of the drum, which has a larger circumferential span than the spacing between adjacent rows of the array, free of the seed pockets.

2. The canola seed sample crusher of claim 1 wherein the seed hopper is movable between a normal position placing its outlet proximate the outer periphery of the drum at the upper periphery thereof, and a dumping position withdrawn away from the drum to release unused seeds from the hopper.

3. The canola seed sample crusher of claim 2 wherein the hopper is biased into the normal position.

4. The canola seed sample crusher of claim 1 further comprising a tape wheel rotatably carried on the frame for rotatably carrying a roll of adhesive tape from which said length of adhesive tape is deployed.

5. The canola seed sample crusher of claim 1 further comprising a tape cutter positioned proximate the pair of crushers at an outlet side thereof to cut free an area of the adhesive tape that carries the crushed seed sample thereon.

6. The canola seed sample crusher of claim 1 further comprising a press wheel rotatably carried on the frame with an outer periphery of the press wheel positioned to urge the adhesive side of the adhesive tape into contact with the sample of canola seed in the seed pockets.

7. The canola seed sample crusher of claim 1 wherein the crushers comprise crushing rollers rotatably carried on the frame in counter-rotating relation to one another with outer peripheries of said crushing rollers in contact or close proximity across the pathway to define a nip through which the adhesive tape is passed to crush the sample of canola seeds thereon.

8. The canola seed sample crusher of claim 1 wherein the array of the seed pockets occupies a grid pattern on the outer periphery of the drum.

9. The canola seed sample crusher of claim 1 further comprising a common drive mechanism shared by the drum and the pair of crushers.

10. The canola seed sample crusher of claim 9 wherein the common drive mechanism comprises a flexible drive member entrained about respective roller elements of the drum and the pair of crushers.

11. The canola seed sample crusher of claim 10 wherein the flexible drive member is a chain and the respective roller elements are sprockets.

12. The canola seed sample crusher of claim 1 further comprising a hand crank operably connected to the drum for manually driven rotation thereof.

13. The canola seed sample crusher of claim 12 wherein the hand crank is operably connected to the drum by a flexible drive member entrained about respective roller elements on rotational shafts of said hand crank and said drum.

14. The canola seed sample crusher of claim 1 further comprising a hand crank operably connected to the pair of crushers for manually driven operation thereof.

15. The canola seed sample crusher of claim 14 wherein the hand crank is attached to a rotational shaft of the pair of crushers for direct drive thereof.

16. The canola seed sample of claim 15 wherein the hand crank is indirectly coupled to the drum for manually driven rotation thereof simultaneously with the pair of crushers.

* * * * *

UNITED STATES PATENT AND TRADEMARK OFFICE
CERTIFICATE OF CORRECTION

PATENT NO. : 10,710,090 B2
APPLICATION NO. : 15/458551
DATED : July 14, 2020
INVENTOR(S) : Gerard Devloo It is certified that error appears in the above-identified patent and that said Letters Patent is hereby corrected as shown below:

In the Claims

In Claim 1, Column 9, Line 35, the expression "forward working" should read --forward working direction--.

Signed and Sealed this
Fourteenth Day of December, 2021

Drew Hirshfeld
*Performing the Functions and Duties of the
Under Secretary of Commerce for Intellectual Property and
Director of the United States Patent and Trademark Office*